United States Patent
Myung

(10) Patent No.: US 11,160,673 B2
(45) Date of Patent: Nov. 2, 2021

(54) STENT HAVING IMPROVED ANTI-MIGRATION FUNCTION

(71) Applicant: BCM Co., Ltd., Gyeonggi-do (KR)

(72) Inventor: Byung Cheol Myung, Gyeonggi-do (KR)

(73) Assignee: BCM Co., Ltd., Gyeonggi-do (KR)

( * ) Notice: Subject to any disclaimer, the term of this patent is extended or adjusted under 35 U.S.C. 154(b) by 44 days.

(21) Appl. No.: 16/199,091

(22) Filed: Nov. 23, 2018

(65) Prior Publication Data
US 2019/0167455 A1   Jun. 6, 2019

(30) Foreign Application Priority Data
Dec. 1, 2017   (KR) .................. 10-2017-0164300

(51) Int. Cl.
| | |
|---|---|
| *A61F 2/848* | (2013.01) |
| *A61F 2/90* | (2013.01) |
| *A61F 2/88* | (2006.01) |
| *A61F 2/852* | (2013.01) |

(Continued)

(52) U.S. Cl.
CPC .............. *A61F 2/88* (2013.01); *A61F 2/848* (2013.01); *A61F 2/852* (2013.01); *A61F 2/90* (2013.01); *A61F 2/07* (2013.01); *A61F 2002/30322* (2013.01); *A61F 2220/0016* (2013.01); *A61F 2220/0075* (2013.01); *A61F 2230/0069* (2013.01); *A61F 2250/0006* (2013.01);
(Continued)

(58) Field of Classification Search
CPC .. A61F 2/852; A61F 2/848; A61F 2/07; A61F 2/90; A61F 2220/0008; A61F 2220/0075; A61F 2230/0069; A61F 2250/0037; A61F 2250/0039; A61F 2250/0063
See application file for complete search history.

(56) References Cited

U.S. PATENT DOCUMENTS 5,064,435 A * 11/1991 Porter ................... A61F 2/90
                                                                606/151
5,916,264 A *  6/1999 Von Oepen .......... A61F 2/07
                                                                623/1.15
(Continued)

FOREIGN PATENT DOCUMENTS

| EP | 2085050 A1 * | 8/2009 | .............. A61F 2/04 |
|---|---|---|---|
| KR | 100455359 | 11/2004 | |

(Continued)

*Primary Examiner* — Paul B Prebilic
(74) *Attorney, Agent, or Firm* — IP & T Group LLP

(57) ABSTRACT

A stent is effective for anti-migration after operation of a lumen, and a first outer stent or a second outer stent is used to be integral to a cylindrical stent and an upper end part of each of the first outer stent or the second outer stent is connected to the cylindrical stent by sutures to have a space part between the cylindrical start, the first outer stent, and the second outer stent. The space part is provided such that the first outer stent or the second outer stent is freely moved or transformed by an external force, and a displacement part caused by the movement or a transformation part caused by the transformation further presses or moves into a lesion part or an inner surface of the lumen to be securely held thereon, whereby the stent is effectively prevented from deviating from the lesion part.

10 Claims, 12 Drawing Sheets

(51) Int. Cl.
*A61F 2/07* (2013.01)
*A61F 2/30* (2006.01)

(52) U.S. Cl.
CPC ............... *A61F 2250/0037* (2013.01); *A61F 2250/0039* (2013.01); *A61F 2250/0063* (2013.01)

(56) References Cited

U.S. PATENT DOCUMENTS

| | | | | |
|---|---|---|---|---|
| 6,099,559 A | * | 8/2000 | Nolting | A61F 2/07 623/1.16 |
| 6,348,066 B1 | * | 2/2002 | Pinchuk | A61F 2/07 606/198 |
| 6,729,356 B1 | * | 5/2004 | Baker | A61B 17/12022 139/383 AA |
| 7,628,804 B2 | * | 12/2009 | Flagle | A61F 2/07 623/1.24 |
| 8,663,314 B2 | * | 3/2014 | Wood | A61F 2/90 623/1.15 |
| 8,690,749 B1 | * | 4/2014 | Nunez | A61M 1/101 600/16 |
| 9,119,713 B2 | * | 9/2015 | Board | A61F 2/2418 |
| 10,588,648 B2 | * | 3/2020 | Brady | A61B 17/221 |
| 10,702,370 B2 | * | 7/2020 | Shu | A61F 2/97 |
| 2001/0049554 A1 | * | 12/2001 | Ruiz | A61F 2/06 623/1.44 |
| 2011/0022151 A1 | * | 1/2011 | Shin | A61F 2/852 623/1.11 |
| 2011/0190905 A1 | * | 8/2011 | Behan | A61F 5/0079 623/23.68 |
| 2011/0282461 A1 | * | 11/2011 | Shin | A61F 2/90 623/23.7 |
| 2011/0319980 A1 | * | 12/2011 | Ryan | A61F 2/07 623/1.16 |
| 2014/0155996 A1 | * | 6/2014 | Wilson | A61F 2/844 623/2.18 |
| 2016/0354201 A1 | * | 12/2016 | Keogh | A61F 2/2418 |
| 2018/0125633 A1 | * | 5/2018 | Fikfak | A61F 2/91 |
| 2020/0214833 A1 | * | 7/2020 | Birmingham | A61F 2/2409 |
| 2020/0315821 A1 | * | 10/2020 | Myung | A61F 2/07 |

FOREIGN PATENT DOCUMENTS

| | | |
|---|---|---|
| KR | 1020120004677 | 1/2012 |
| KR | 101171075 | 8/2012 |
| KR | 101657648 | 9/2016 |

* cited by examiner

STENT HAVING IMPROVED ANTI-MIGRATION FUNCTION

CROSS REFERENCE TO RELATED APPLICATION

The present application claims priority to Korean Patent Application No. 10-2017-0164300, filed Dec. 1, 2017, the entire contents of which is incorporated herein for all purposes by this reference.

BACKGROUND OF THE INVENTION

Field of the Invention

The present invention generally relates to a stent having an improved anti-migration function. More particularly, the present invention relates to a stent having an improved anti-migration function, wherein the stent manufactured by interweaving superelastic shape memory alloy wires is configured to have a double structure such that an outer stent is held on an inner surface of a lumen of the human body, thereby preventing migration of the stent and preventing the stent from pricking an inner surface of the lumen due to the facility of the insertion or removal of the stent into or from the lumen.

Description of the Related Art

Generally, when stenosis occurs due to tumors or other reasons in lumens of the human body, including digestive organs such as a duodenum, a biliary tract, and an esophagus, urinary organs such as a urethra, and respiratory organs such as a trachea, the human body cannot perform its normal functions. Accordingly, a stent is inserted into the stenotic portion in a lumen of a human body to expand the stenotic portion so that the human body can function normally.

The stent includes a hollow stent body formed by interweaving at least one superelastic shape memory alloy wire diagonally such that the wire alternately crosses over and under itself to form a plurality of diamond-shaped spaces in the hollow stent body, so that the hollow stent body applies tension to inner and outer sides of a lumen to expand the stenotic portion.

However, the conventional stent described above is composed of the hollow stent body alone, and has a problem in that due to activities such as coughing or food intake, the stent tends to move in a lumen of a human body to easily deviate from a lesion part into which the stent is implanted.

To address the problem of the conventional stent, various stents having an anti-migration structure have been presented.

First, as in patent documents 1 and 2, at least one of opposite ends of a hollow stent body has an expanded part in such a manner that the expanded part is slanted or has steps, so that the stent is brought into close contact with an inner surface of the lumen of the human body to prevent the migration thereof.

However, the stent has a limitation in that it is not able to completely realize the anti-migration effect because the stent cannot have an expanded part on at least one of opposite ends of the hollow stent body considering a manufacturing condition of the stent, and even if it is possible to manufacture an expanded part, the expanded part alone cannot ensure the stent to be securely held on the inner surface of a lumen of the human body.

Second, as in patent document 3, a stent is provided with an anti-migration bent part formed in such a manner that a wire is extended to slantingly protrude upward at multiple positions on an outer circumference of a hollow stent body, and thus the anti-migration bent part is held to an inner surface of a lumen in a human body, thereby preventing migration of the stent.

However, since it is difficult to produce an anti-migration bent part on the outer circumference of the hollow stent body, the stent has a problem in that production of the stent is inefficient, and it is not easy to operate successfully due to the growing volume of the stent from the use of an additional wire while the anti-migration bent part is produced. Though it is not problematic to insert the stent into a lumen of a human body since the anti-migration bent part slantingly protrudes in an opposite direction to which the stent is inserted into the lumen of the human body, when the stent is removed from the lumen, an end of the anti-migration bent part tends to bend back to prick an inner surface of the lumen in the human body. Accordingly, the stent has a problem in that it is difficult to remove from the lumen, and thus may lead to damage of the inner surface of the lumen in the human body upon removal.

To address the problems, in patent document 4, a superelastic shape memory alloy wire is diagonally interwoven such that the wire alternately crosses over and under itself, and a rod is placed and held underneath the wire and heated to form an anti-migration bent part of a rod shape protruded from the wire so as to prevent migration of the stent. However, since the anti-migration bent part is diagonally provided, the anti-migration bent part cannot be securely supported by the inner surface of the lumen.

DOCUMENTS OF RELATED ART (Patent Document 1) Korean Patent No. 10-0455359;
(Patent Document 2) Korean Patent Application Publication No. 10-2012-0004677;
(Patent Document 3) Korean Patent No. 10-1171075; and
(Patent Document 4) Korean Patent No. 10-1657648.

SUMMARY OF THE INVENTION

Accordingly, the present invention has been made keeping in mind the above problems occurring in the related art, and the present invention is intended to propose a stent having an improved anti-migration function, wherein an inner stent and an outer stent are configured to have different shapes and be combined with each other, and the outer stent is displaced in any pressing direction relative to an operation position by pressing of an inner surface of a lumen, or an initial shape of the outer stent may be transformed by the pressing, whereby a portion of the displaced outer stent or a transformation part transformed from the initial shape is held on the inner surface of the lumen or a lesion part, and further presses or moves into the inner surface of the lumen or the lesion part so as to be held on any portion of the lumen or the lesion part, which prevents the stent from deviating from a position of the lumen being operated on.

In order to achieve the above object, according to one aspect of the present invention, there is provided a stent having an improved anti-migration function, wherein a cylindrical stent formed by interweaving superelastic shape memory alloy wires diagonally such that the wires alternately cross over and under each other is connected to the outer stent having a shape of a predetermined angle and being narrow in an upper side and wide in a lower side on one end of the cylindrical stent by sutures so as to have a space part between the cylindrical stent and the outer stent, and the outer stent is moved from an operation position or an initial shape thereof is transformed by the pressing of an inner surface of a lumen of the human body, whereby a portion of the displaced outer stent or a transformation part transformed from the initial shape further presses or moves into the inner surface of the lumen so as to be held on any portion of the lumen or a lesion part, thereby preventing the stent from deviating from a position of the lumen being operated on.

According to the present invention, a first outer stent 2 and/or a second outer stent 4 is used to be integral to the cylindrical stent 1 and just an upper end part of each of the first outer stent 2 and/or the second outer stent 4 is connected to the cylindrical stent 1 by the sutures 3 so as to have the space part between the cylindrical stent 1, the first outer stent 2, and the second outer stent 4.

According to the present invention, the space part 5 is provided such that the first outer stent 2 and/or the second outer stent 4 is freely moved or transformed on the cylindrical stent 1 by an external force, and a displacement part 24 caused by the movement and/or the transformation part 34 caused by the transformation further presses or moves into the lesion part 31 or the inner surface of the lumen 30 at a position thereof so as to be securely held on the lesion part 31 or the inner surface of the lumen 30, or the transformation part 34 further presses or moves into the lesion part 31 or the inner surface of the lumen 30 at the position thereof so as to be securely held on the lesion part 31 or the inner surface of the lumen 30.

Accordingly, the outer stent is further moved or transformed by the movement of the lumen or the lesion part due to the movement of a human body. Accordingly, the outer stent further moves into or presses the lumen or the lesion part, thereby effectively preventing the stent from deviating from the lesion part.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
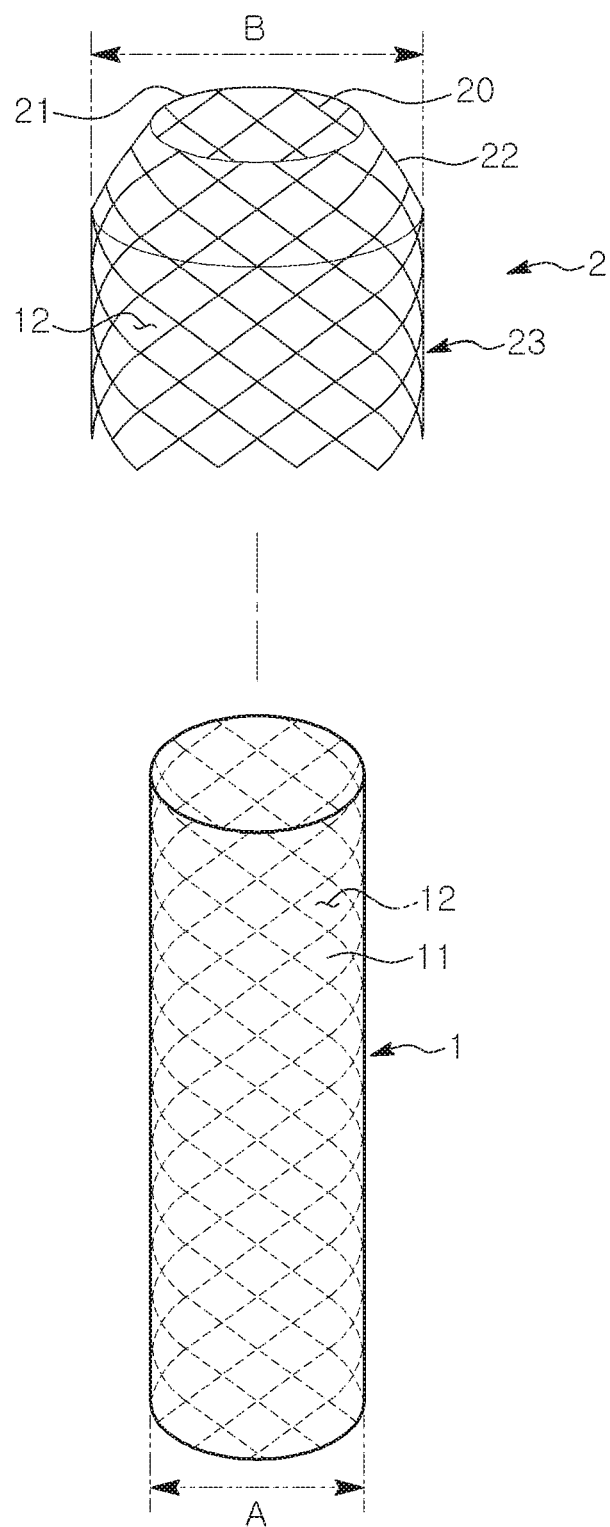
FIG. 1 is an exploded perspective view according to an embodiment of the present invention.

Hereinbelow, a basic configuration of the present invention will be described based on FIGS. 1 and 2.

As the conventional method, a cylindrical stent 1 is provided by interweaving superelastic shape memory alloy wires, and an outer stent 2 is also provided by interweaving the superelastic shape memory alloy wires. A bent part 22 is provided by being bent from an upper end 21 of the outer stent 2 at a predetermined interval L so as to have a diameter B larger than a diameter A of the cylindrical stent 1, and a cylindrical body part 23 is provided beneath the bent part so as to have the diameter B larger than the diameter A of the cylindrical stent 1. In this case, the cylindrical stent 1 and the outer stent 2 are connected to each other on the end parts 10, 20 by sutures 3 so as to be integral to each other.

A space part 5 is defined between the cylindrical stent 1 and the outer stent 2 by the connection.

Figure 3:
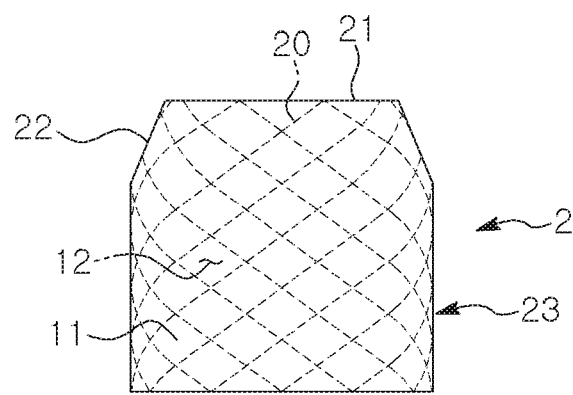
FIGS. 3 to 5 are views showing shapes according to the embodiment of the present invention.
Figure 4:
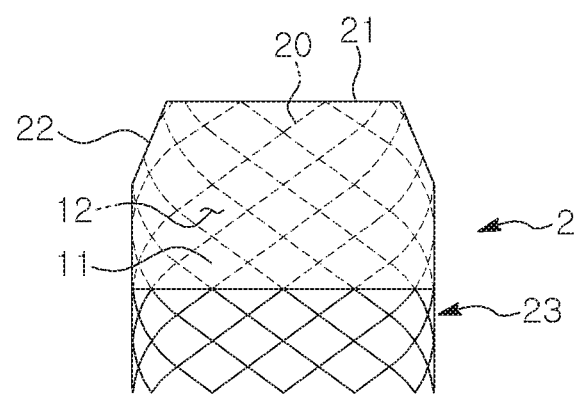
Figure 5:
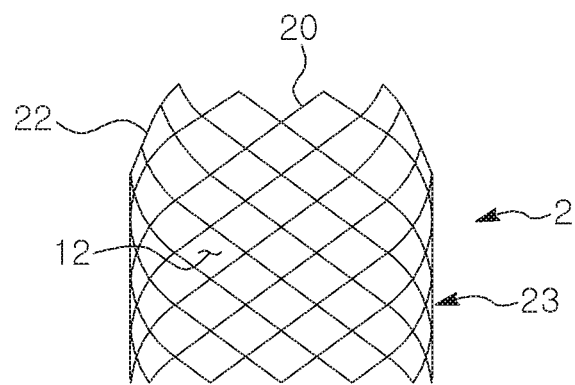

Furthermore, the cylindrical stent 1 is configured to have a membrane part 11 made of silicon or PTFE provided thereon so as to cover all diamond-shaped parts 12 of an entirety of the cylindrical stent 1 as the conventional method, and as shown in FIGS. 3 to 5, when required, the outer stent 2 may be configured to have the membrane part 11 made of silicon or PTFE provided thereon so as to cover all diamond-shaped parts 12 of an entirety of the outer stent 2 as the conventional method, or may be configured to have the membrane part 11 made of the silicon or PTFE provided thereon so as to cover all diamond-shaped parts 12 of a predetermined portion of the outer stent 2 as the conventional method, or when required, may not include the membrane part 11.

A reference number 50, which is not described, refers to a pulling string to be used when a stent is removed after an operation.

Now operation of the present invention will be described.

Figure 2:
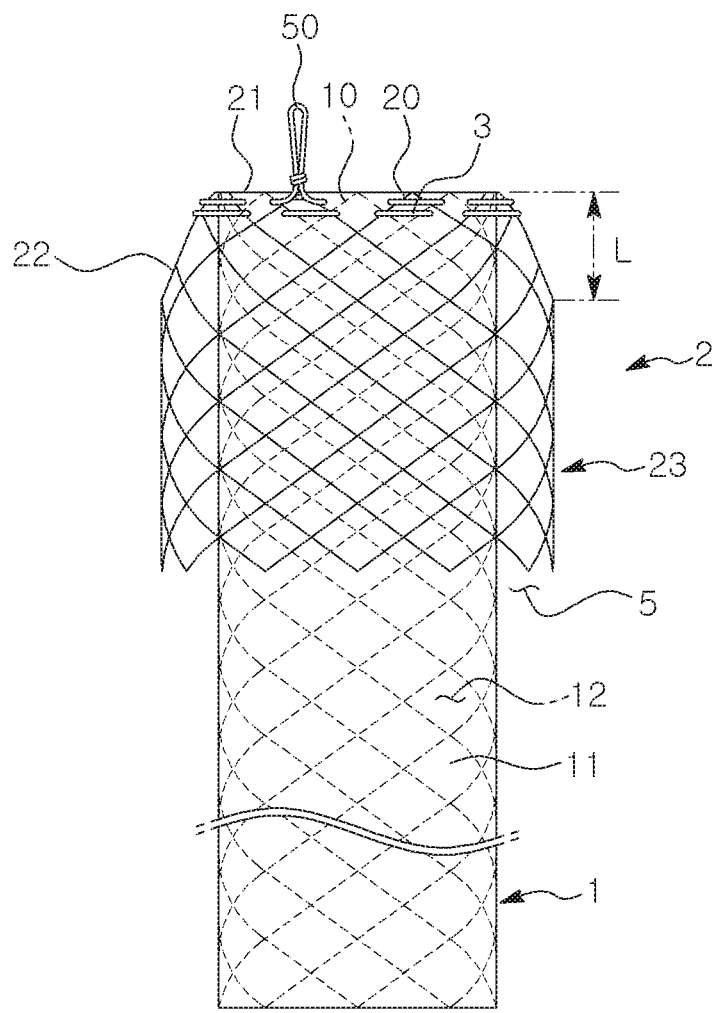
FIG. 2 is a combined state view according to the embodiment of the present invention.
Figure 6:
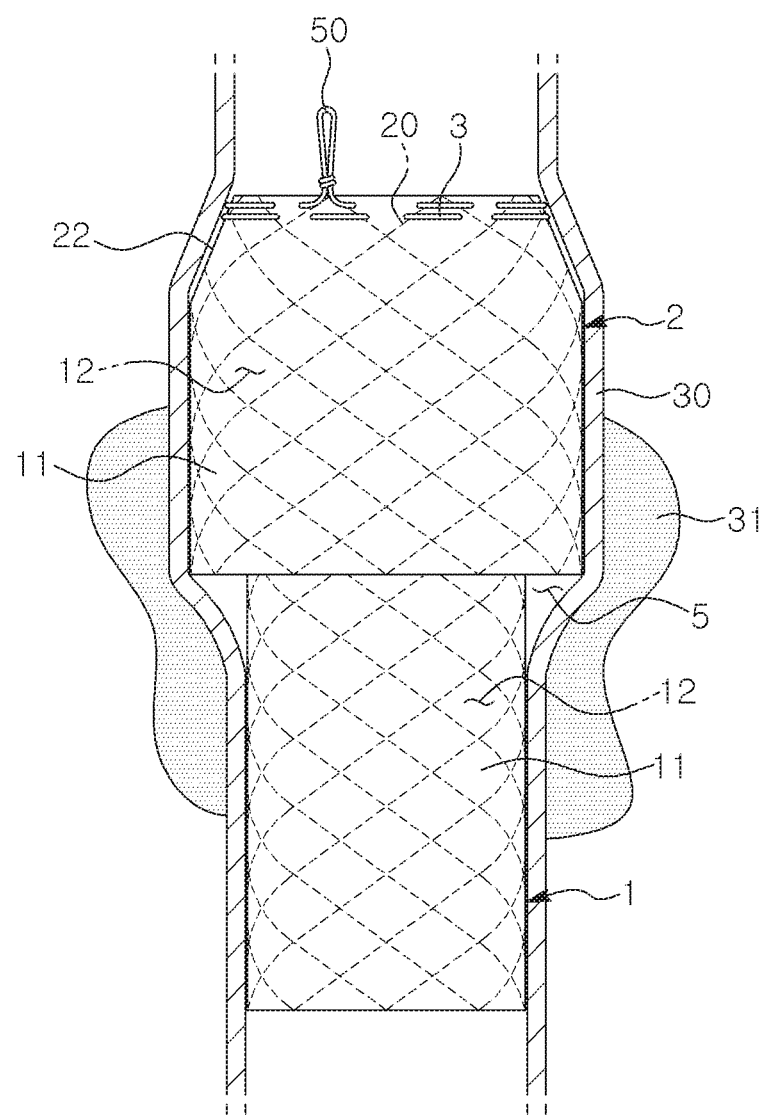
FIG. 6 is a reference view showing the state of an operation according to the embodiment of the present invention.

The stent having an improved anti-migration function that has a configuration as shown in FIGS. 1 and 2 is positioned at a lesion part 31 of a lumen 30 for an operation by a catheter known as a conventional stent transfer system as shown in FIG. 6.

Figure 7:
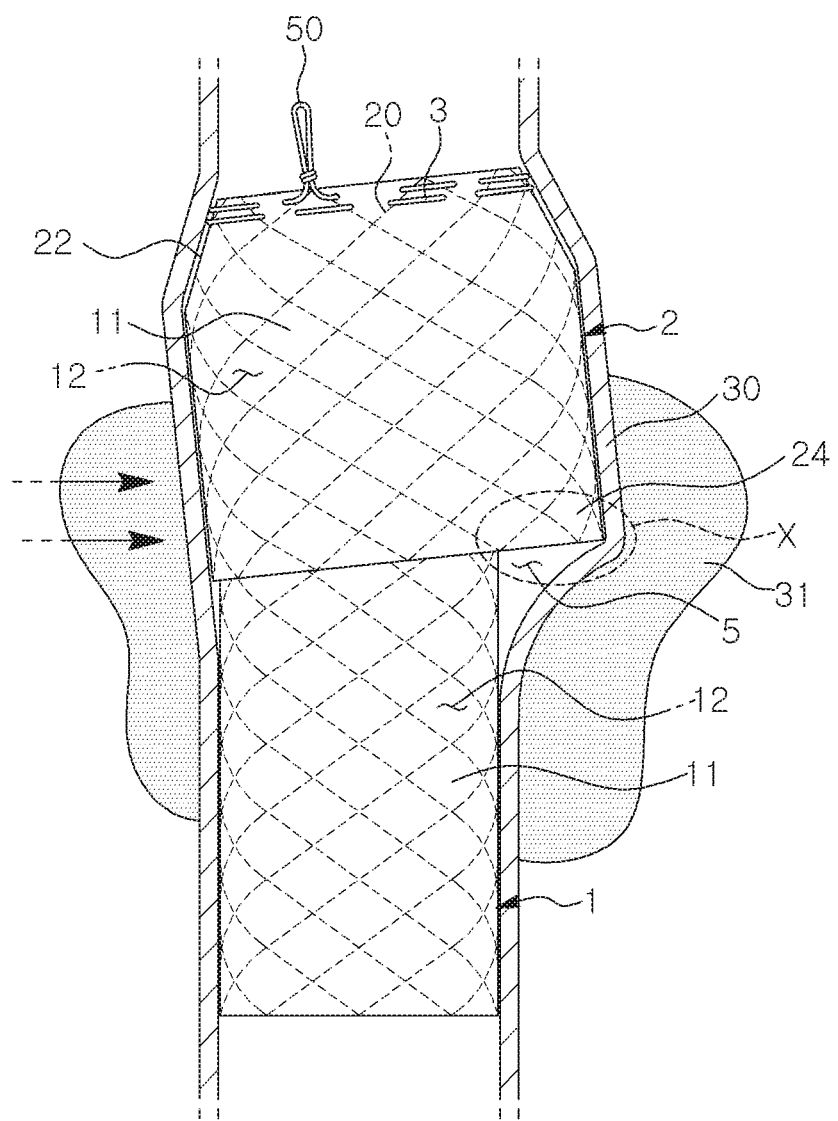
FIGS. 7 and 8 are views showing operation states according to the embodiment of the present invention.
Figure 8:
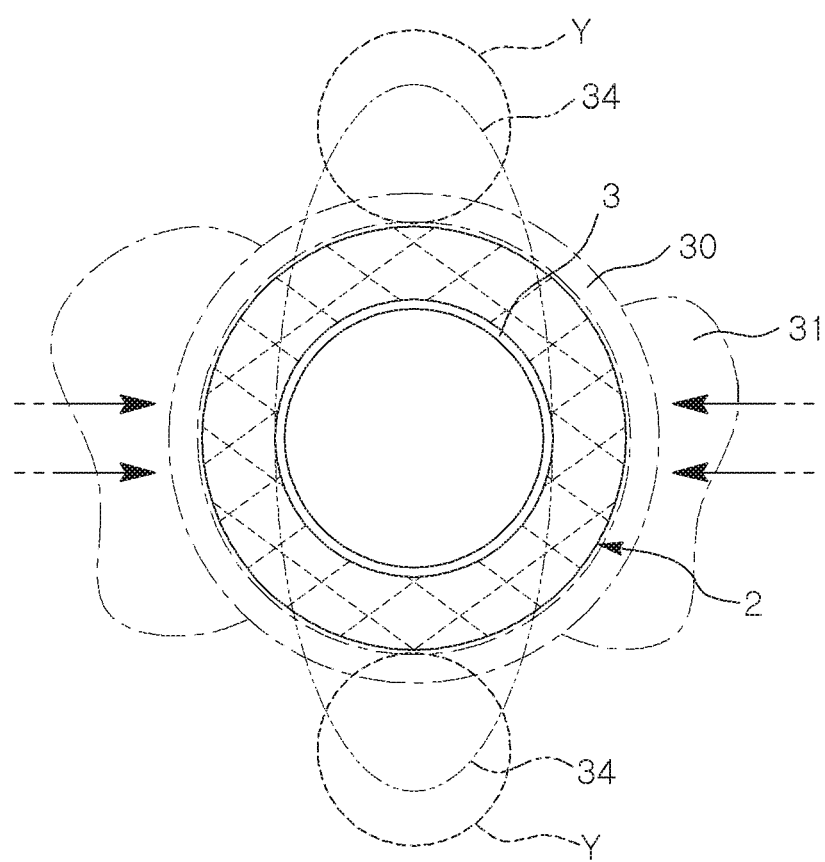

When the operation is performed, the lesion part 31 or the lumen 30 is moved by a movement of a human body, and the outer stent 2 positioned at the lesion part is pressed by the movement of the lumen 30 or the lesion part 31. As shown in FIGS. 7 and 8, the end of the outer stent 2 is connected to the cylindrical stent 1 and the space part 5 is defined between the cylindrical stent 1 and the outer stent 2. Accordingly, a lower part of the outer stent 2 is displaced in a pressing direction relative to the end part 20 at which the outer stent 2 is connected to the cylindrical stent 1 by pressing due to the movement of the lumen 30 or the lesion part 31, or when the outer stent 2 is in close contact with the lumen 30 or the lesion part 31 at a position opposite to a position of the displaced lower part, the outer stent 2 cannot move and an initial shape thereof is transformed.

A portion of the outer stent 2 at a side opposite to a side at which the outer stent 2 is pushed is displaced in a pushing direction thereof by a portion of the outer stent being pushed and so a large displacement space part X is provided. Furthermore, the portion of the outer stent 2 is more displaced in any one direction to have the displacement part 24 and the displacement part 24 further presses or moves into the lesion part 31 or an inner surface of the lumen 30 at a position thereof so as to be securely held on the lesion part 31 or the inner surface of the lumen 30 (see FIG. 7).

Furthermore, when the outer stent 2 at a side opposite to a side to which the outer stent 2 is displaced is in close contact with the lumen 30 or the lesion part 31 due to the pressing of the lesion part 31 or the lumen 30, the outer stent 2 cannot move and as shown in FIG. 8, while the initial shape of the outer stent 2 is transformed from a circular shape into an oval shape, a large transformation space part Y is provided to have a transformation part 34. The transformation part 34 further presses or moves into the lesion part 31 or the inner surface of the lumen 30 at the position thereof so as to be securely held on the lesion part 31 or the inner surface of the lumen 30 (see FIG. 8).

According to the present invention, when required, the outer stent 2 may include a multiplicity of outer stents so as to be connected to the cylindrical stent 1 by the sutures 3.

Figure 9:
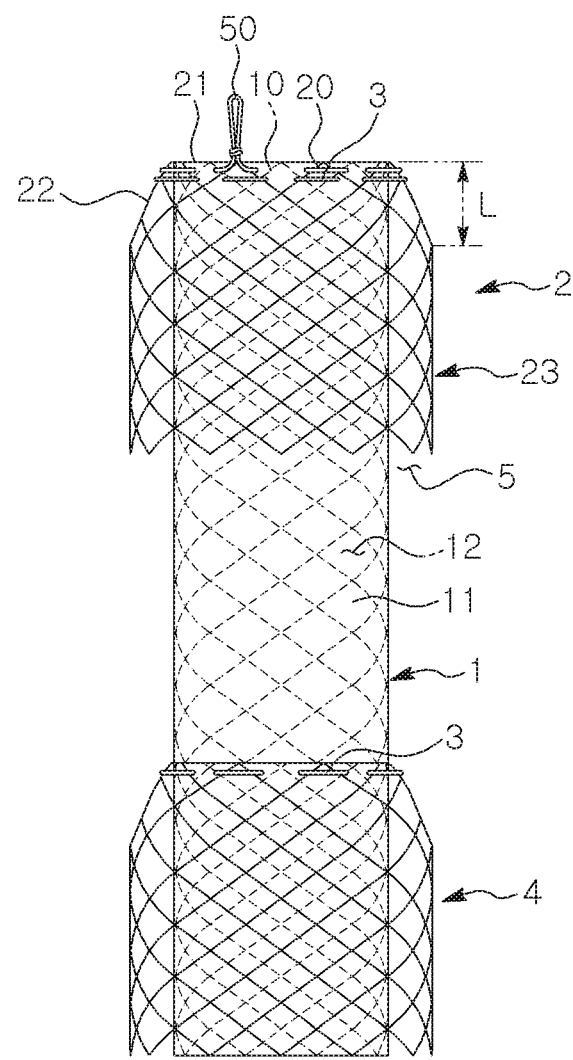
FIGS. 9 to 17 are views of other embodiments of the present invention.

As shown In FIG. 9, while a cylindrical stent 1 and a first outer stent 2 are connected to each other on end parts 10, 20 thereof by sutures 3 so as to be integral to each other, an additional second outer stent 4 provided on a middle portion of the cylindrical stent 1 and having the same structure as a structure of the first outer stent 2 may be connected to the cylindrical stent 1 on an upper end of the additional second outer stent 4 by the sutures 3 so as to be integral to the cylindrical stent 1 such that a lower end part of the cylindrical stent 1 and a lower end part of the second outer stent 4 is positioned at the same position.

In this case, since using at least two second outer stents 4 being integral to the cylindrical stent 1 rather than one outer stent 2 being integral to the cylindrical stent 1 multiplies an operation of the one outer stent 2, anti-migration function may be multiplied to the extent that the second outer stents are added.

Figure 10:
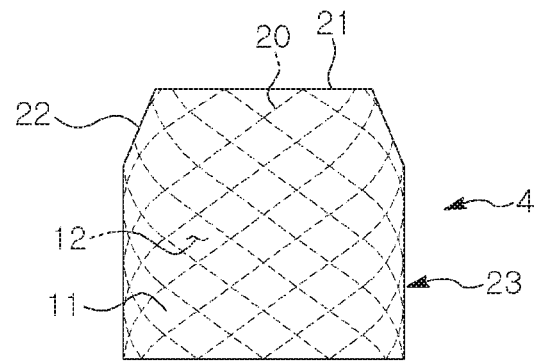
Figure 11:
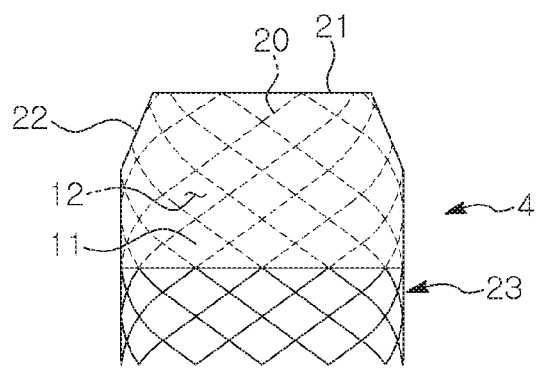
Figure 12:
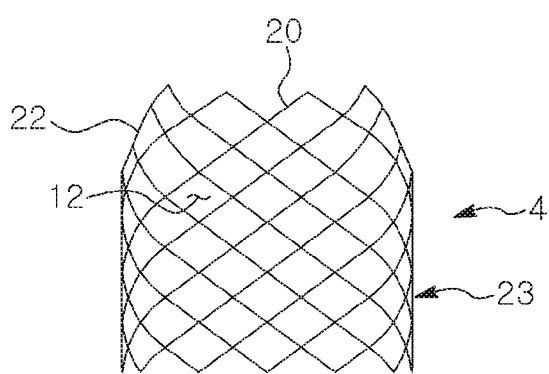

In this case, as shown in FIGS. 10 to 12, when required, the second outer stent 4 may be configured to have a membrane part 11 made of silicon or PTFE provided thereon so as to cover all diamond-shaped parts 12 of an entirety of the second outer stent 4 as the conventional method, or may be configured to have the membrane part 11 made of the silicon or PTFE provided thereon so as to cover all diamond-shaped parts 12 of a predetermined portion of the second outer stent 4 as the conventional method, or when required, may not include the membrane part 11.

Figure 13:
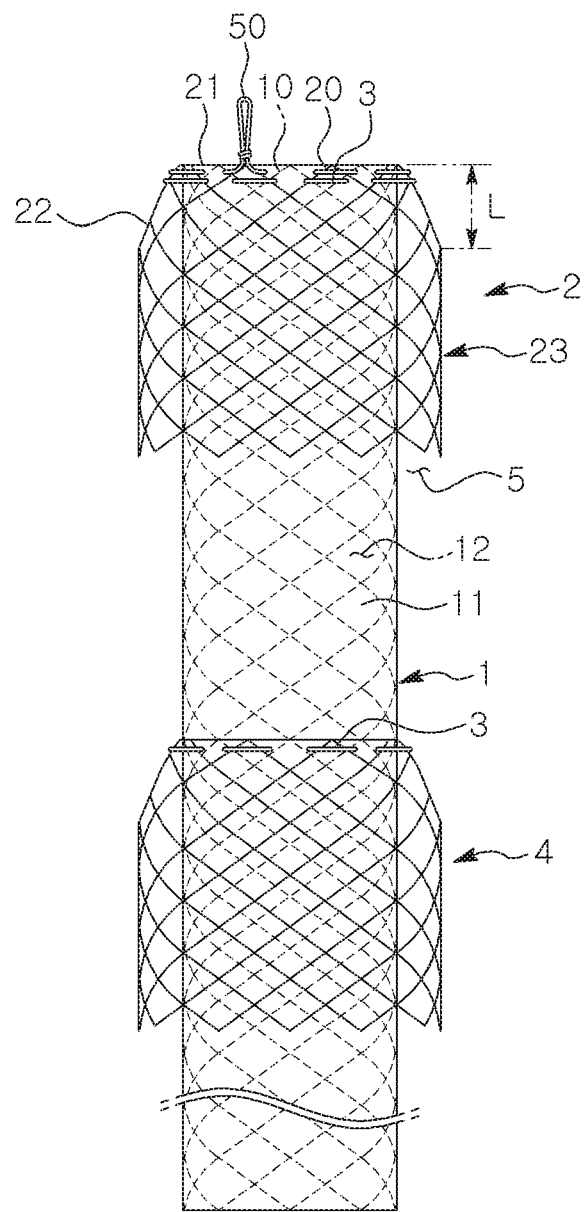
Figure 14:
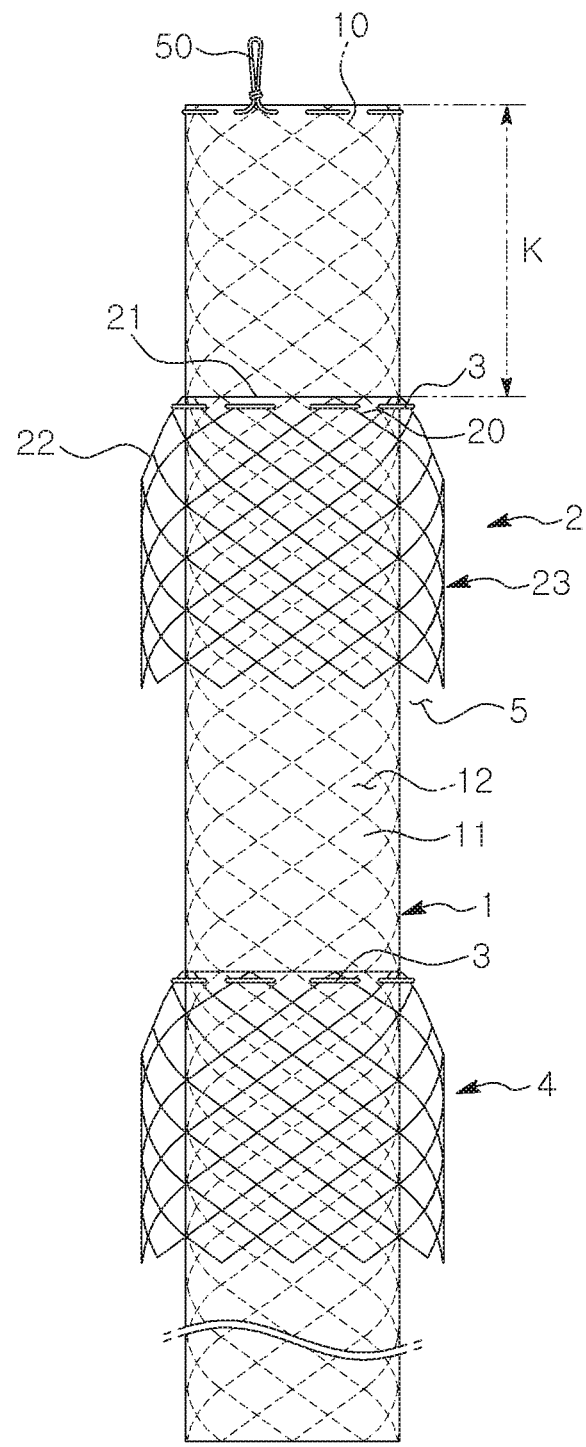

In addition, as shown in FIG. 13, according to the present invention, while the cylindrical stent 1 and the first outer stent 2 are connected to each other on the end parts 10, 20 thereof by the sutures 3 so as to be integral to each other, an additional second outer stent 4 may be connected to the cylindrical stent 1 on a middle portion of the cylindrical stent 1 by the sutures 3 so as to be integral thereto such that the lower end part of the cylindrical stent 1 exposed to an outside of the second outer stent 4 is long.

In this case, using at least two second outer stents 4 being integral to the cylindrical stent 1 rather than one outer stent 2 being integral to the cylindrical stent 1 multiplies an operation of the outer stent 2, which multiplies anti-migration function to the extent that the second outer stents are added, and is suitable when the lesion part is large or a length of a lumen to be operated on is long In this case, as shown in FIGS. 10 to 12, when required, the second outer stent 4 may be configured to have the membrane part 11 made of silicon or PTFE provided thereon so as to cover all diamond-shaped parts 12 of the entirety of the second outer stent 4 as the conventional method, or may be configured to have the membrane part 11 made of the silicon or PTFE provided thereon so as to cover all diamond-shaped parts 12 of the predetermined portion of the second outer stent 4 as the conventional method, or when required, may not include the membrane part 11.

As mentioned above, the first outer stent 2 is connected to an upper end part of the cylindrical stent 1. That is, the cylindrical stent 1 and the first outer stent 2 are connected to each other on the end parts 10, 20 by the sutures so as to be integral to each other. However, as shown in 14, with the first outer stent 2 being spaced apart from the upper end part of the cylindrical stent 1 at a predetermined interval K, the cylindrical stent 1 and the first outer stent 2 may be connected to each other by the sutures 3 so as to be integral to each other.

This shows that various embodiments of the present invention are possible as the upper end part of the cylindrical stent 1 is spaced apart from the first outer stent 2 at the predetermined interval K.

This also shows that the various embodiments can be selectively used according to characteristics such as a length or a shape of the lumen, or a shape of a lesion part.

Figure 15:
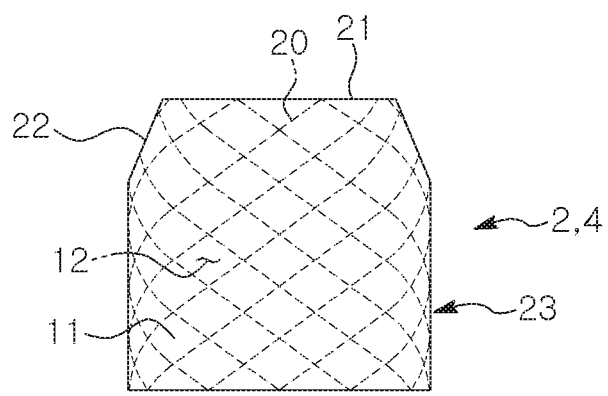
Figure 16:
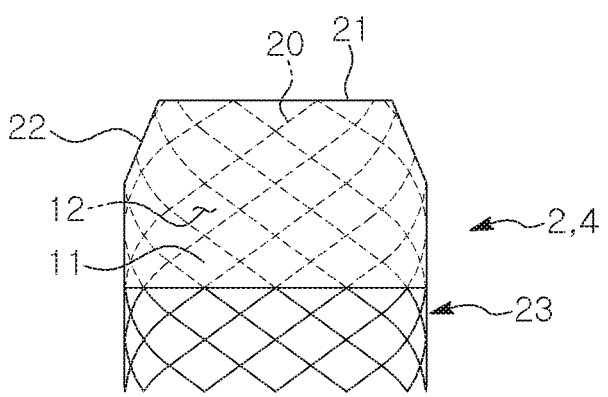
Figure 17:
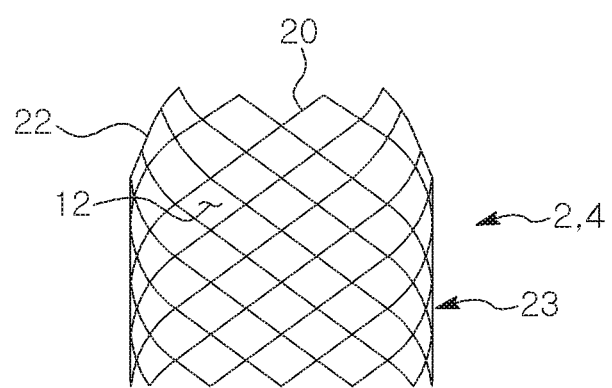

In this case, the second outer stent 4 may be connected to the cylindrical stent 1 by the sutures 3 so as to be integral to the cylindrical stent 1. In addition, as shown in FIGS. 15 to 17, the first outer stent 2 and the second outer stent 4, which are selectively connected to the cylindrical stent 1, may be configured to have the membrane part 11 made of silicon or PTFE provided thereon so as to cover all diamond-shaped parts 12 of entireties of the first outer stent 2 and the second outer stent 4 as the conventional method, or may be configured to have the membrane part 11 made of silicon or PTFE provided thereon so as to as cover all diamond-shaped parts 12 of a predetermined portion of the first outer stent 2 and the second outer stent 4 as the conventional method, or when required, may not include the membrane part 11.

As described above, according to the present invention, the first outer stent 2 and/or the second outer stent 4 is used to be integral to the cylindrical stent 1 and just the upper end of each of the first outer stent 2 and/or the second outer stent 4 is connected to the cylindrical stent 1 by using the sutures 3 to have a space part 5 between the cylindrical stent 1, the first outer stent 2, and the second outer stent 4.

According to the present invention, the space par 5 is provided such that the first outer stent 2 and/or the second outer stent 4 is freely moved or transformed on the cylindrical stent 1 by am external force, and a displacement part 24 due to the movement and/or the transformation part 34 due to the transformation further presses or moves into the lesion part 31 or the inner surface of the lumen 30 at a position thereof so as to be securely held on the lesion part 31 or the inner surface of the lumen 30, or the transformation part 34 further presses or moves into the lesion part 31 or the inner surface of the lumen 30 at the position thereof so as to be securely held on the lesion part 31 or the inner surface of the lumen 30.

Accordingly, the outer stent is further moved or transformed by the movement of the lumen or the lesion part due to the movement of a human body. Accordingly, the outer stent further moves into or presses the lumen or the lesion part, thereby effectively preventing the stent from deviating from the lesion part.

What is claimed is:
1. A stent having an improved anti-migration function, the stent comprising:
   a cylindrical stent formed by interweaving superelastic shape memory alloy wires;
   an outer stent including a bent part bent from an upper end thereof at a predetermined interval so as to have a diameter larger than a diameter of the cylindrical stent, and a cylindrical body part provided beneath the bent part and having a diameter that is larger than the diameter of the cylindrical stent, wherein the outer stent excluding from a portion of the bent part is not in close contact with the cylindrical stent; and
   a space part defined between the cylindrical stent and the outer stent by connecting one end of the outer stent to an upper edge of the cylindrical stent by sutures, wherein a predetermined portion of the outer stent is covered by a membrane and a remaining portion of the outer stent is not covered by the membrane and thereby has openings through the interwoven alloy wires, wherein, along an axial length of the cylindrical body part, the cylindrical body part is structured to contact a lumen or a lesion part so as to be securely held against the lesion part or against an inner surface of the lumen, and wherein around the connected end of the outer stent by pressing caused by movement of the lumen or the lesion part, a lower part of the outer stent is displaced and moved in any pressing direction and a portion of the outer stent is more displaced to have a displacement part, and an opposite side of the displacement part is in close contact with the lumen or the lesion part to form a transformation part, a shape of which is transformed into an oval shape by the pressing.

2. The stent of claim 1, wherein the cylindrical stent has a membrane part provided thereon so as to cover the cylindrical stent.

3. The stent of claim 1, wherein the outer stent has a membrane part provided thereon so as to cover a predetermined portion of the outer stent.

4. The stent of claim 1, wherein the outer stent does not include a membrane part.

5. The stent of claim 1, wherein the outer stent has a membrane part provided thereon so as to cover an entirety of the outer stent.

6. A stent having an improved anti-migration function, the stent comprising:
a cylindrical stent formed by interweaving superelastic shape memory alloy wires;
a first outer stent and a second outer stent having the same structure, the second outer stent including a bent part bent from an upper end thereof at a predetermined interval so as to have a diameter larger than a diameter of the cylindrical stent and a cylindrical body part provided beneath the bent part and having the diameter larger than the diameter of the cylindrical stent; and
a space part defined between the cylindrical stent, the first outer stent and the second outer stent by connecting an upper end of the first outer stent to an upper edge of the cylindrical stent by sutures and the upper end of the second outer stent to the cylindrical stent by sutures, with the first outer stent and the second outer stent being spaced apart from each other at a predetermined interval, wherein a predetermined portion of the outer stent is covered by a membrane and a remaining portion of the outer stent is not covered by the membrane and thereby has openings through the interwoven alloy wires, wherein, along an axial length of the cylindrical body part, the cylindrical body part is structured to contact a lumen or a lesion part so as to be securely held against the lesion part or against an inner surface of the lumen, and wherein around the connected end of the first outer stent by pressing caused by movement of the lumen or the lesion part, a lower part of the first outer stent is displaced and moved in any pressing direction and a portion of the first outer stent is more displaced to have a displacement part, and an opposite side of the displacement part is in close contact with the lumen or the lesion part to form a transformation part, a shape of which is transformed into an oval shape by the pressing.

7. The stent of claim 6, wherein the second outer stent is connected to the cylindrical stent when a lower end part of the second outer stent is located at the same position as a position of a lower end part of the cylindrical stent.

8. The stent of claim 6, wherein the second outer stent is connected to the cylindrical stent, with a lower end part of the cylindrical stent exposed to an outside at a lower part of the second outer stent.

9. The stent of claim 6, wherein the cylindrical stent has a membrane part provided thereon so as to cover the cylindrical stent.

10. The stent of claim 6, wherein any one of the first outer stent or the second outer stent has a membrane part provided thereon so as to cover a predetermined portion of any one of the first outer stent or the second outer stent.

* * * * *